(12) United States Patent
Freeman et al.

(10) Patent No.: US 6,766,042 B2
(45) Date of Patent: Jul. 20, 2004

(54) SYSTEM TO AUTOMATICALLY DETECT EYE CORNEAL STRIAE

(75) Inventors: James F. Freeman, Memphis, TN (US); Roy E. Williams, Collierville, TN (US)

(73) Assignee: Memphis Eye & Contact Associates, Memphis, TN (US)

( * ) Notice: Subject to any disclaimer, the term of this patent is extended or adjusted under 35 U.S.C. 154(b) by 660 days.

(21) Appl. No.: 09/842,539

(22) Filed: Apr. 26, 2001

(65) Prior Publication Data

US 2002/0159618 A1 Oct. 31, 2002

(51) Int. Cl.[7] .................................................. G06K 9/00
(52) U.S. Cl. ........................................ 382/128; 348/78
(58) Field of Search ........................... 382/128, 117, 382/199, 168, 170; 348/78; 351/205, 211, 212; 128/922; 600/476

(56) References Cited

U.S. PATENT DOCUMENTS

| | | | |
|---|---|---|---|
| 4,685,140 A | 8/1987 | Mount, II .................... 382/6 |
| 4,707,647 A | 11/1987 | Coldren et al. ............. 318/568 |
| 4,977,605 A | 12/1990 | Fardeau et al. .............. 382/51 |
| 4,995,716 A | 2/1991 | Warnicki et al. ........... 351/212 |
| 5,054,907 A | 10/1991 | Sklar et al. ................. 351/212 |
| 5,549,597 A | 8/1996 | Shimmick et al. ............ 606/5 |
| 5,697,945 A | 12/1997 | Kritzinger et al. ......... 606/161 |
| 5,764,345 A | 6/1998 | Fladd et al. ............... 356/35.5 |
| 5,779,711 A | 7/1998 | Kritzinger et al. ......... 606/107 |
| 5,864,383 A | 1/1999 | Turner et al. ............... 351/212 |
| 5,934,285 A | 8/1999 | Kritzinger et al. ......... 128/898 |
| 6,007,202 A | 12/1999 | Apple et al. ................ 351/209 |
| 6,019,754 A | 2/2000 | Kawesch ....................... 606/4 |
| 6,023,530 A | 2/2000 | Wilson ....................... 382/219 |
| 6,070,981 A | 6/2000 | Mihashi et al. ............ 351/212 |
| 6,099,522 A | 8/2000 | Knopp et al. ................. 606/10 |
| 6,116,738 A | 9/2000 | Rorabaugh .................. 351/247 |
| 6,213,605 B1 | 4/2001 | D'Souza et al. ............ 351/212 |
| 6,264,328 B1 | 7/2001 | Williams et al. ........... 351/221 |
| 6,275,718 B1 | 8/2001 | Lempert ..................... 600/407 |
| 6,299,307 B1 | 10/2001 | Oltean et al. ............... 351/210 |
| 2002/0159619 A1 * | 10/2002 | Callies et al. ............... 382/128 |
| 2002/0159620 A1 * | 10/2002 | Williams et al. ............ 382/128 |
| 2002/0159621 A1 * | 10/2002 | Callies et al. ............... 382/128 |

FOREIGN PATENT DOCUMENTS

| WO | WO 9710487 A1 | 3/1997 | ............ G01B/9/02 |
|---|---|---|---|
| WO | WO 00/56204 A1 | 9/2000 | ............ A61B/3/117 |

OTHER PUBLICATIONS

Webpage downloaded Feb. 10, 2000 for "Striae in Optical Glass—The Unseen Problem" at http://www.optsd.org/ansi_op/stria.html, 1 page.
Webpage downloaded Mar. 6, 2000 for "Folds and Striae" at http://www.cibavision.com/text/prosight/management-guide/B03.folds.html, 1 page.
Article on "LASIK light helps locate debris on the cornea," by Steven Siepser, MD, in *Slack, Inc.* Electronic newsletter, Oct. 15, 1998. Retrieved from http://www.slackinc.com/eye/osn/199810b/light.asp., 2 pages.
Article on "Modified technique successfully removes flap wrinkles, reduces striae," by Alexander Hatsis, MD, in *Slack, Inc.* Electronic newsletter, Apr. 15, 1999. Retrieved from http://www.slackinc.com/eye/osn/, 4 pages.

* cited by examiner

*Primary Examiner*—Andrew W. Johns
(74) *Attorney, Agent, or Firm*—Gordon & Jacobson, P.C.

(57) ABSTRACT

An automated eye corneal striae detection system for use with a refractive laser system includes a cornea illuminator, a video camera interface, a computer, and a video display for showing possible eye corneal striae to the surgeon. The computer includes an interface to control the corneal illuminator, a video frame grabber which extracts images of the eye cornea from the video camera, and is programmed to detect and recognize eye corneal striae. The striae detection algorithm finds possible cornea striae, determines their location, or position, on the cornea and analyzes their shape. After all possible eye corneal striae are detected and analyzed, they are displayed for the surgeon on an external video display. The surgeon can then make a determination as to whether the corneal LASIK flap should be refloated, adjusted or smoothed again.

56 Claims, 12 Drawing Sheets

SYSTEM TO AUTOMATICALLY DETECT EYE CORNEAL STRIAE

CROSS REFERENCES TO RELATED APPLICATIONS

Not applicable.

BACKGROUND

1. Field of Invention

The present invention relates to ophthalmic surgical procedures for the correction of refractive error. More particularly, the present invention relates to an ophthalmic refractive correction procedure known as LASIK, wherein a corneal flap is produced. Still more particularly, the present invention relates to an ophthalmic instrument and method which automates the detection of eye corneal striae, or corneal wrinkles, following the LASIK procedure.

2. Description of Prior Art

Laser refractive surgery has become a very popular method for providing patients with better vision. The majority of laser refractive surgery patients will have the procedure termed LASIK (Laser In-Situ Keratomileusis) performed. There are some very important advantages that have caused LASIK to be used over the original Photo-Refractive Keratectomy (PRK) technique. For example, the healing process is usually shorter and more comfortable for the patient and larger refractive corrections can be performed.

In the LASIK procedure a microkeratome device is used to create a thin "flap," typically 120 to 160-microns in depth, in order to expose the corneal stroma below. The flap is not cut completely across the cornea, thus leaving a hinge. The flap is gently lifted off the cornea and held to the side while the laser system delivers the treatment profile into the cornea stroma (tissue directly underneath the flap). After the laser delivery is completed, the flap is put back in place and smoothed by the surgeon. Within about 2 minutes, the flap is reattached enough such that the lid speculum, which is used to hold the eye open, may be removed. At this point the laser refractive procedure is completed.

Although this procedure does possess many advantages over PRK, it has one drawback that can cause postoperative refractive problems for the patient. This drawback is termed corneal flap striae, which is basically a wrinkle in the corneal flap, created when the flap is not uniformly reattached to the cornea. This striae, or wrinkle, can cause vision problems in the patient ranging from glare to acuity problems due to irregular astigmatism.

Presently, there are two approaches to reducing or eliminating eye corneal striae. The first approach is a preventative method. Here, in one approach, inventors have developed methods and tools to visibly mark the cornea before the LASIK flap is made. These markings are then used to realign the flap when it is put back in place. U.S. Pat. No. 5,934,285 (1999) and U.S. Pat. No. 5,697,945 (1997) both to Kritzinger, et. al. describe tools that provide various visible markings to aid in realignment. However, even this approach does not guarantee that there will be no striae present nor does it automate the detection of striae. In another approach, U.S. Pat. No. 6,019,754 to Kawesch, describes a method to improve flap adherence, by applying filtered compressed air to the corneal flap. Again, it only addresses flap adherence; it does not address the detection of eye corneal striae.

The second current approach attempts to detect striae after the flap has been put back in place. Currently, there are two dominant methods for attempting to detect striae after the LASIK procedure. Both are manual, as opposed to automated, techniques performed by the surgeon. In the most popular method, the refractive surgeon checks the "smoothness" of the cornea, with just the operating microscope and the diffuse, broadband, white light source present with the operating surgical microscope. Here, the surgeon is just making a broad visual determination if striae is present. In a second less popular, but more effective method, the surgeon uses a handheld slit lamp, which projects a thin line of visible broadband, white light onto the cornea. The surgeon scans this line across the cornea and looks for aberrations, or edges, on what otherwise should be a smooth surface. Usually, only two to three scans are made at different angles on the cornea and thus striae can be, and often are, missed at the other angles that are not addressed.

Neither of these two present approaches for reducing or eliminating eye corneal striae addresses the automatic detection of eye corneal striae following LASIK refractive surgery.

Outside the ophthalmic area, U.S. Pat. No. 5,764,345 to Fladd, et. al., presents a method for detecting inhomogeneities, specifically striae, in infused silica glasses. This technique was developed for cases where a sample, such as a glass optical lens, can have a beam of light passed through it such that an instrument on the other side of the lens can detect it. This detector is part of an expensive interferometer system used to measure the striae present in the glass. This approach would not work for eye corneal striae detection as one cannot place a detector on the other side of the cornea. Additionally, the interferometer requires precise alignment and would be too expensive for this application.

Thus, there is no present method for automatically detecting eye corneal striae following LASIK refractive surgery.

SUMMARY

The present invention overcomes many of the problems associated with existing manual methods and tools used to prevent and detect eye corneal striae, or corneal wrinkles, after LASIK refractive surgery, by automating the eye corneal striae detection process with a computer-based analysis system.

OBJECTS AND ADVANTAGES

It is therefore an object of the invention to provide an automated technique for detecting eye corneal striae after LASIK refractive surgery which is more precise and more complete than existing manual techniques.

It is another object of the invention to provide an automated technique for detecting eye corneal striae after LASIK refractive surgery which is faster than existing manual techniques.

It is a further object of the invention to provide an automated technique for detecting eye corneal striae after LASIK refractive surgery which will aid in the reduction of patient revisits to correct eye corneal striae problems.

It is an additional object of the invention to provide an automated technique for detecting eye corneal striae after LASIK refractive surgery which is capable of being retrofit to existing refractive laser systems without modifying any hardware in the existing laser system.

In accord with these objects an automated eye corneal striae detection system is provided for use with a refractive laser system which produces a laser for surgically reshaping the eye. The automated eye corneal striae detection system includes a means for illuminating the cornea of the eye, a means for capturing images of the eye, a computer, and a video display to present possible corneal striae to the surgeon. The means for illuminating the cornea preferably includes an apparatus for concentrating multiple beams of light at predetermined points comprising a ring shaped housing with a plurality of annularly arranged spaced opens. Within the housing at each opening is a holder for a light source for a beam of light, preferably monochromatic, directed out of the opening. A cover for the housing, preferably encasing a diffusing optical element, is threadably engaged with the latter. The computer preferably includes a digital input-output printed circuit board which controls the illuminating apparatus; a video frame grabber which captures images from a camera on the laser system; and is programmed to perform an automated eye corneal striae detection algorithm with respect to the images. The automated eye corneal striae detection algorithm finds possible striae in the image and calculates their position and shape characteristics. The possible striae are then displayed on the video display so that the surgeon can make a determination as to whether the corneal flap should be refloated, adjusted or smoothed again.

The automated eye corneal striae detection system may be retrofit to existing refractive laser systems. Additionally, the automated eye corneal striae detection system may be provided as an integral part of new refractive laser surgery systems.

Additional objects and advantages of the invention will become apparent to those skilled in the art upon reference to the detailed description taken in conjunction with the accompanying drawings.

Figure 1:
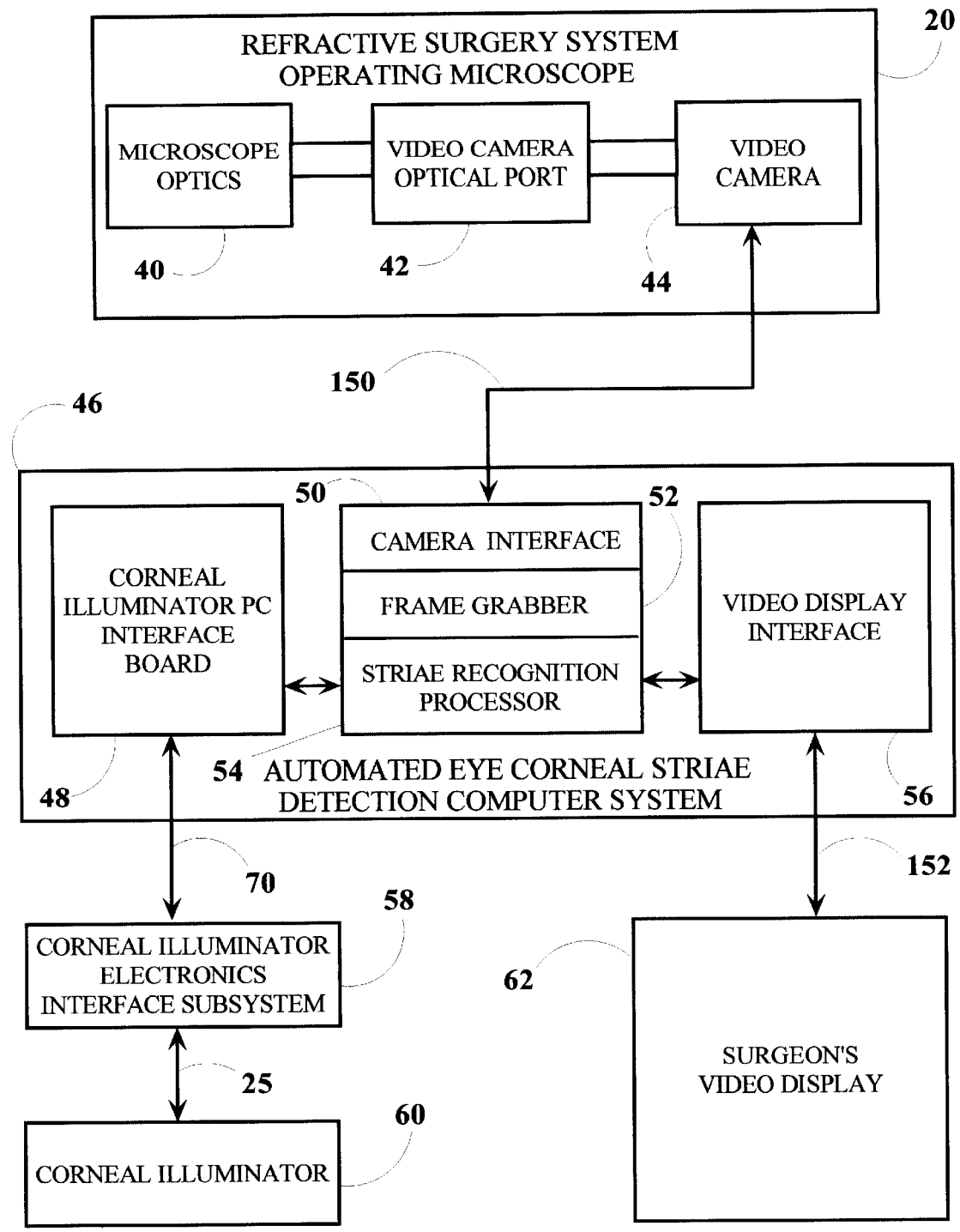
FIG. 1 is a schematic view of a refractive surgery system microscope provided with a corneal illuminator, an automated eye corneal striae detection computer system, and a surgeon's video display of the invention.

Reference Numerals in Drawings 20 refractive surgery system operating microscope
21 annularly arranged openings
22 ring illuminator housing
23 diffuser cover
24 illumination light sources
25 corneal illuminator interface cable
26 light source beams
27 pupil
28 cornea
29 eye
30 illumination coverage area one
31 iris
32 illumination coverage area two
34 illumination coverage area three
36 illumination coverage area four
40 microscope optics
42 video camera optical port
44 video camera
46 automated eye corneal striae detection computer system
48 corneal illuminator PC interface board
50 video camera interface
52 frame grabber
54 eye corneal striae recognition processor
56 video display interface
58 corneal illuminator electronics interface subsystem
60 corneal illuminator
62 surgeon's video display
70 interface cable
72 optocouplers
74 electrical current limiting resistors
80 Automated Eye Corneal Striae Detection Algorithm
82 Turn ON LEDs
84 Send ON Signal to Control Electronics
86 Receive Digitized Image
88 mask out striae area in image
90 apply nonlinear edge detection operator
92 apply thresholding technique
94 apply outer gradient operator
96 apply particle filter
98 get particle parameters from particle filter
100 all areas processed (decision activity)?
102 outline possible corneal striae
104 show possible coneal striae on display
106 process digital image again (decision activity)?
108 detection algorithm done
120 illumination light source printed circuit board
122 illuminator interface connector port
124 clearance space
126 mounting fasteners
128 mounting holes
130 diffuser cover mounting holes
132 illumination light source printed circuit board (PCB) clearance holes
134 large clearance hole (in PCB)
136 region-of-interest (ROI)
138 eye optical axis
140 mounting bracket
142 video camera lens
144 alternative fiber optic corneal illuminator electronics interface subsystem
146 fiber optic corneal illuminator interface bundle
148 fiber optic illumination light sources 150 video camera cable
152 video display cable
160 pattern matching technique
162 get matched particle parameters

PREFERRED EMBODIMENT—DESCRIPTION

Turning now to FIG. 1, a refractive surgery system operating microscope 20 is coupled to an automated eye corneal striae detection computer system 46 of the invention. Refractive surgery system operating microscope 20 includes a set of microscope optics 40 to allow the surgeon adequate view of the corneal surface and a video camera optical port 42 that optically couples the image the surgeon views to a video camera 44, e.g., a Sony XC-75, that is used to capture the corneal image seen in FIG. 5. An automated eye corneal striae detection computer system 46, e.g., a Compaq Deskpro EN, 450-MHz PC, generally includes a video camera interface 50 which is coupled to the video-out port of video camera 44 through a video camera cable 150, a frame grabber 52, e.g., a National Instruments PCI 1408, a video display interface 56 which is coupled to a surgeon's video display 62 through a video display cable 152, a corneal illuminator PC interface board 48, e.g., a National Instruments PCI-6503, and an eye corneal striae recognition processor 54, preferably implementing a software algorithm described in FIG. 4. A corneal illuminator electronics interface subsystem 58, connected to corneal illuminator PC interface board 48 through an interface cable 70, provides the necessary electrical current (amperage) to a corneal illuminator 60 through a corneal illuminator interface cable 25 in order to adequately illuminate the cornea.

Figure 2A:
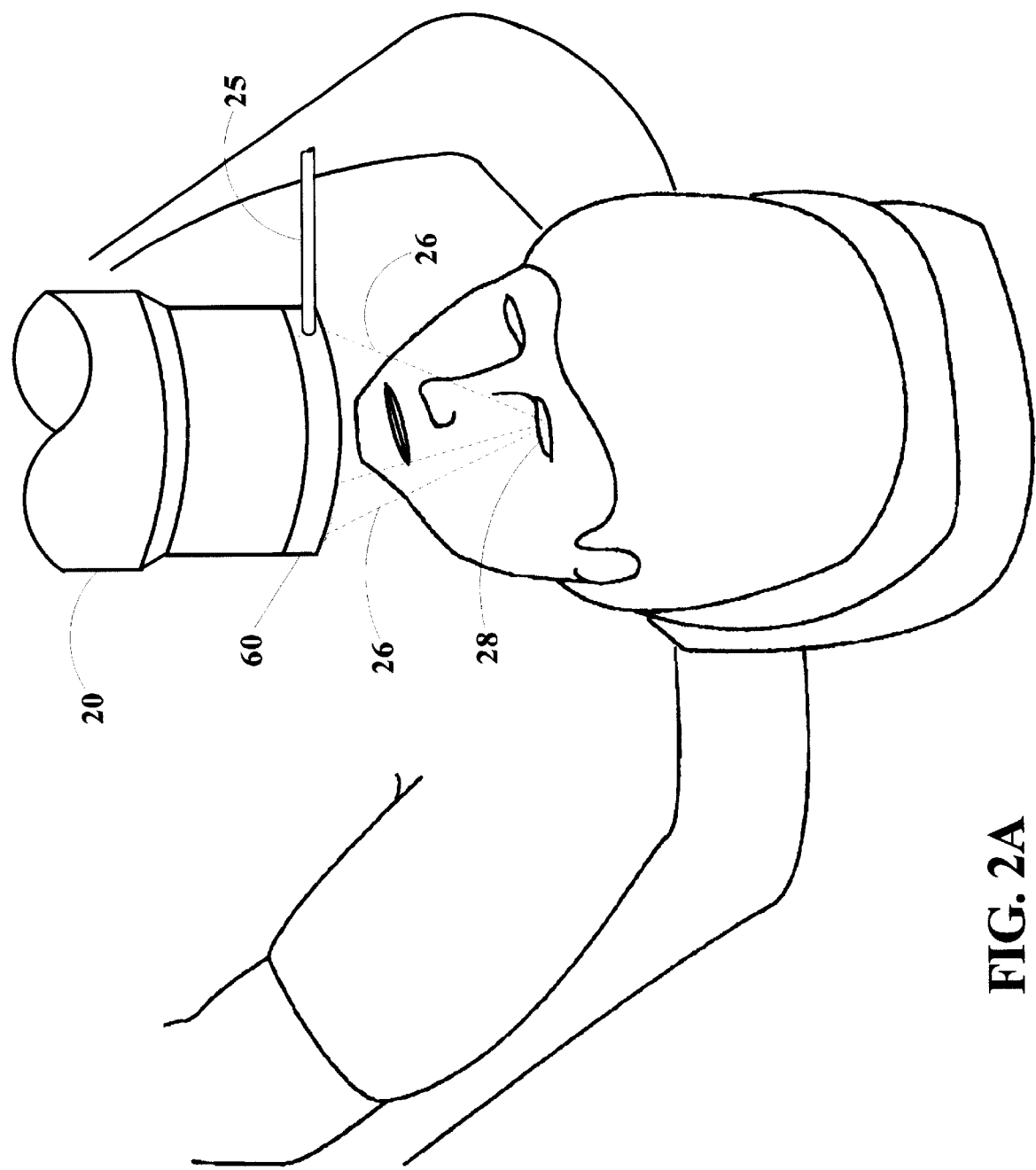
FIG. 2A is a perspective view of a lighting system for illuminating the eye following laser vision correction treatment provided in accordance with the principles of the embodiment of the invention and shown attached to a refractive surgery system microscope disposed above an eye being analyzed.
Figure 3:
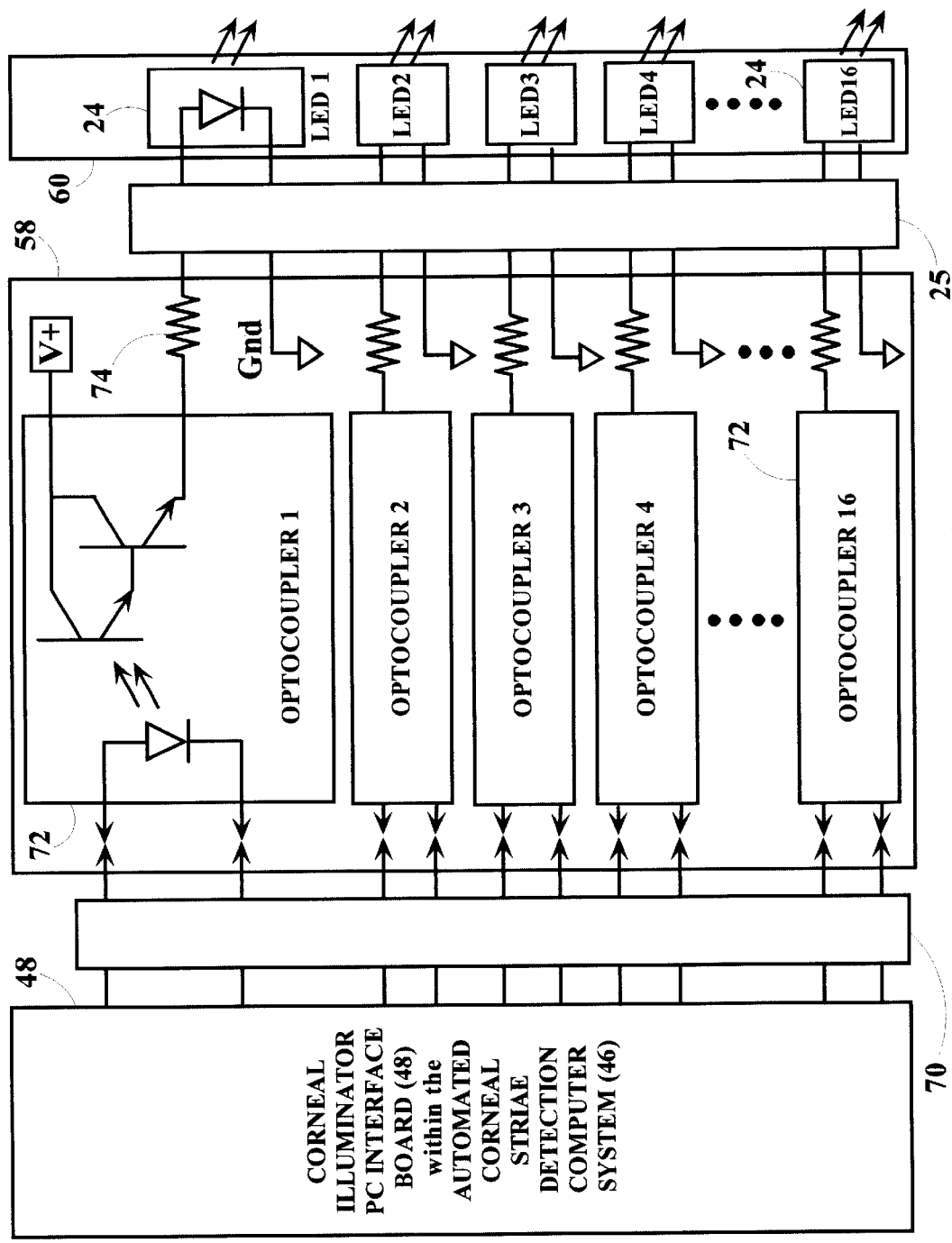
FIG. 3 is a schematic view of the corneal illuminator electronics interface subsystem of the invention.

In FIG. 2A, corneal illuminator 60, attached to refractive surgery system operating microscope 20, is shown in relationship to a patient's cornea 28. A plurality of light source beams 26 are shown projected onto cornea 28. Corneal illuminator interface cable 25 connects corneal illuminator 60 to corneal illuminator electronics interface subsystem 58 (FIGS. 1, 3).

Figure 2B:
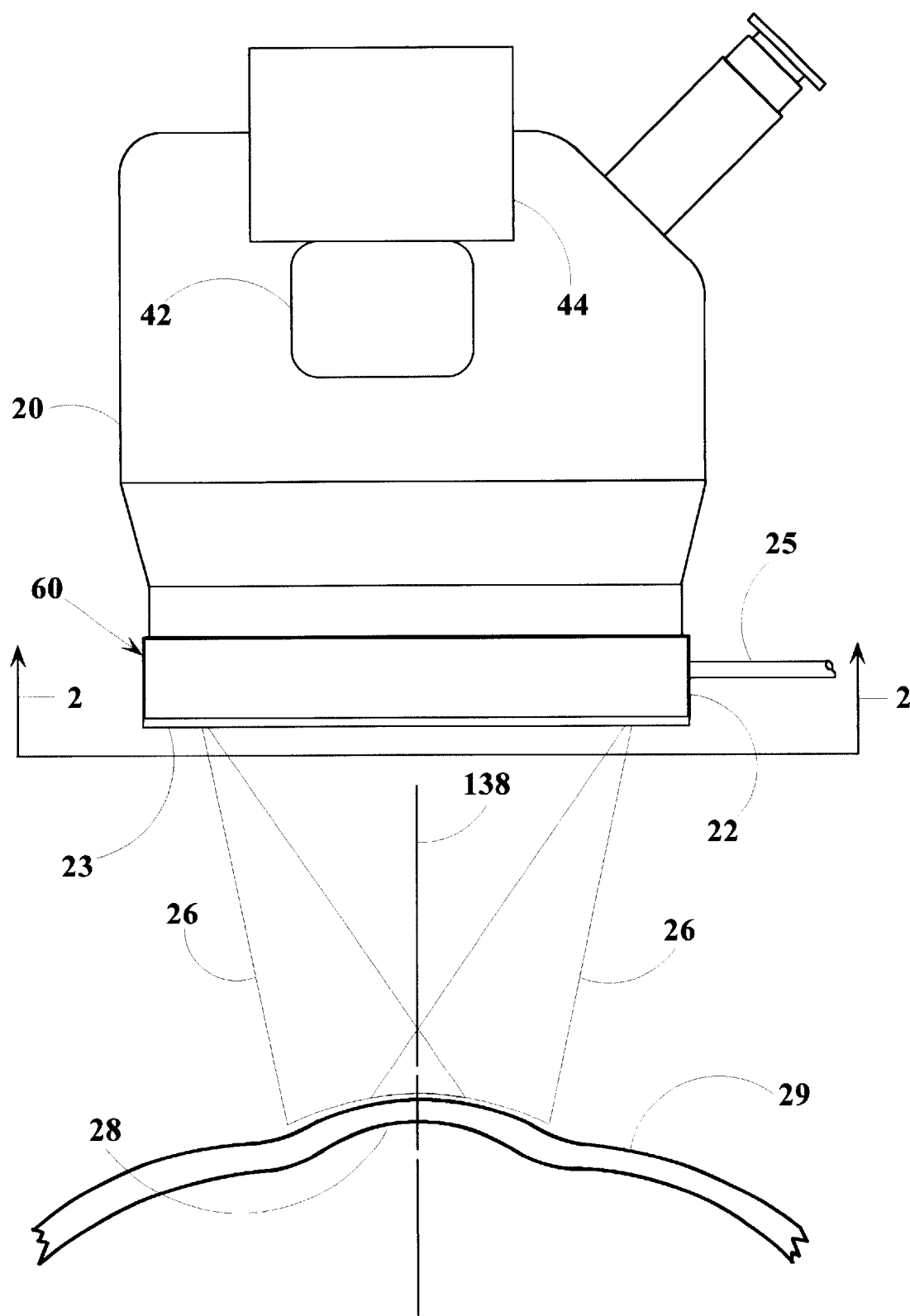
FIG. 2B is a schematic elevation view showing the lighting system of this invention juxtaposed with a microsurgery microscope and the surface of the eye and additionally showing the light beams directed to the cornea.
Figure 5:
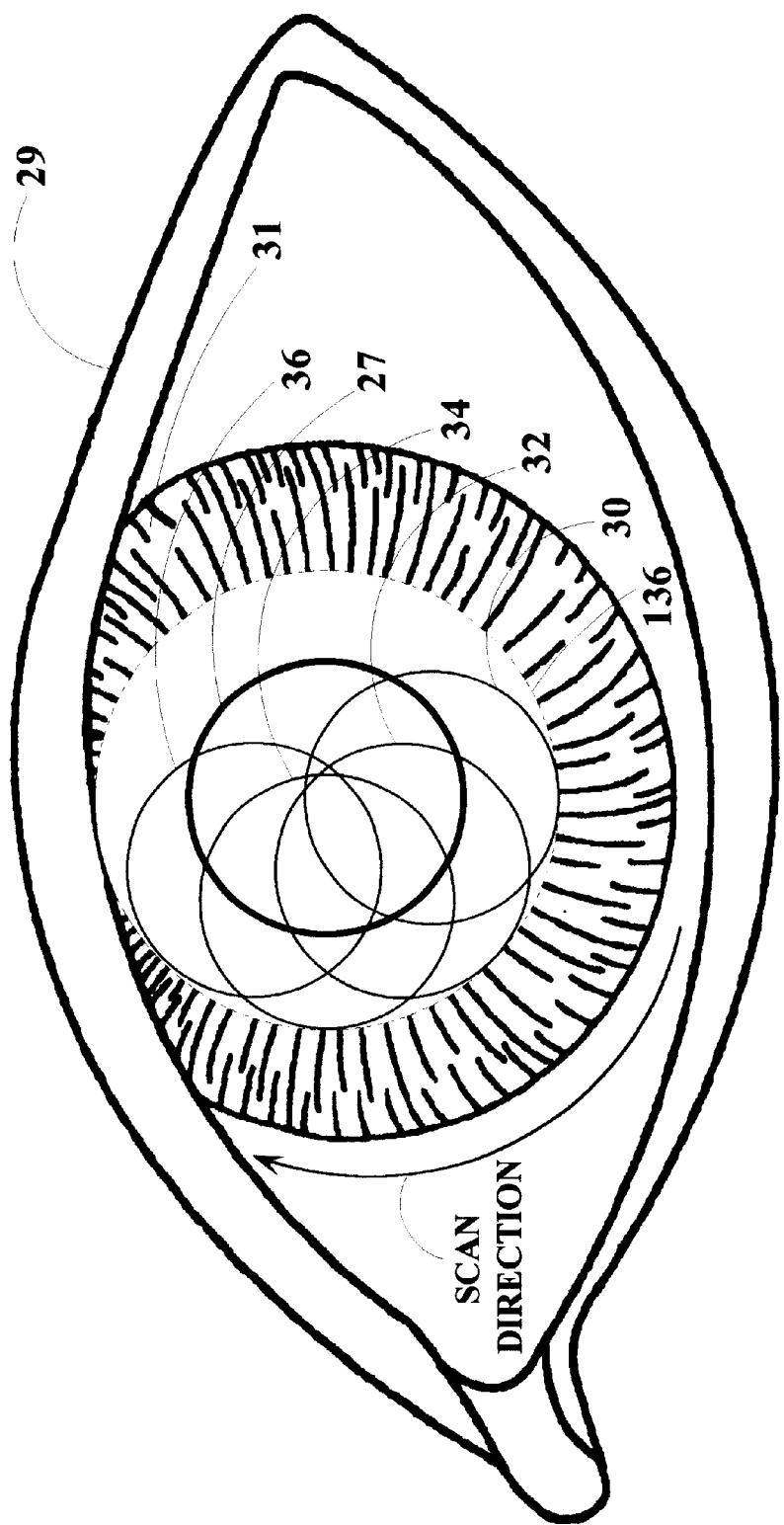
FIG. 5 shows the process of scanning the light beams around the cornea during the analysis portion of the invention.

In FIG. 2B, corneal illuminator 60, which is a combination of a ring illuminator housing 22 and a diffuser cover 23, is shown coupled to refractive surgery system operating microscope 20. Corneal illuminator interface cable 25 connects corneal illuminator 60 to corneal illuminator electronics interface subsystem 58 (FIGS. 1, 3). Light source beams 26 are shown directed through diffuser cover 23, containing a diffusing material particular to the monochromatic wavelength used, e.g., for the preferred embodiment a Tech Spec™ linear polarizing laminated film is preferred, which is mounted over a plurality of illumination light sources 24 (FIG. 2C) and attaches to ring illuminator housing 22. Light source beams 26 are directed to cornea 28 which is part of an eye 29 that has undergone LASIK refractive surgery. In the described embodiment, light source beams 26 are directed toward cornea 28 at a 16-degree angle from eye optical axis 138. Other angles may be used with different illumination coverage areas (FIG. 5).

Figure 2C:
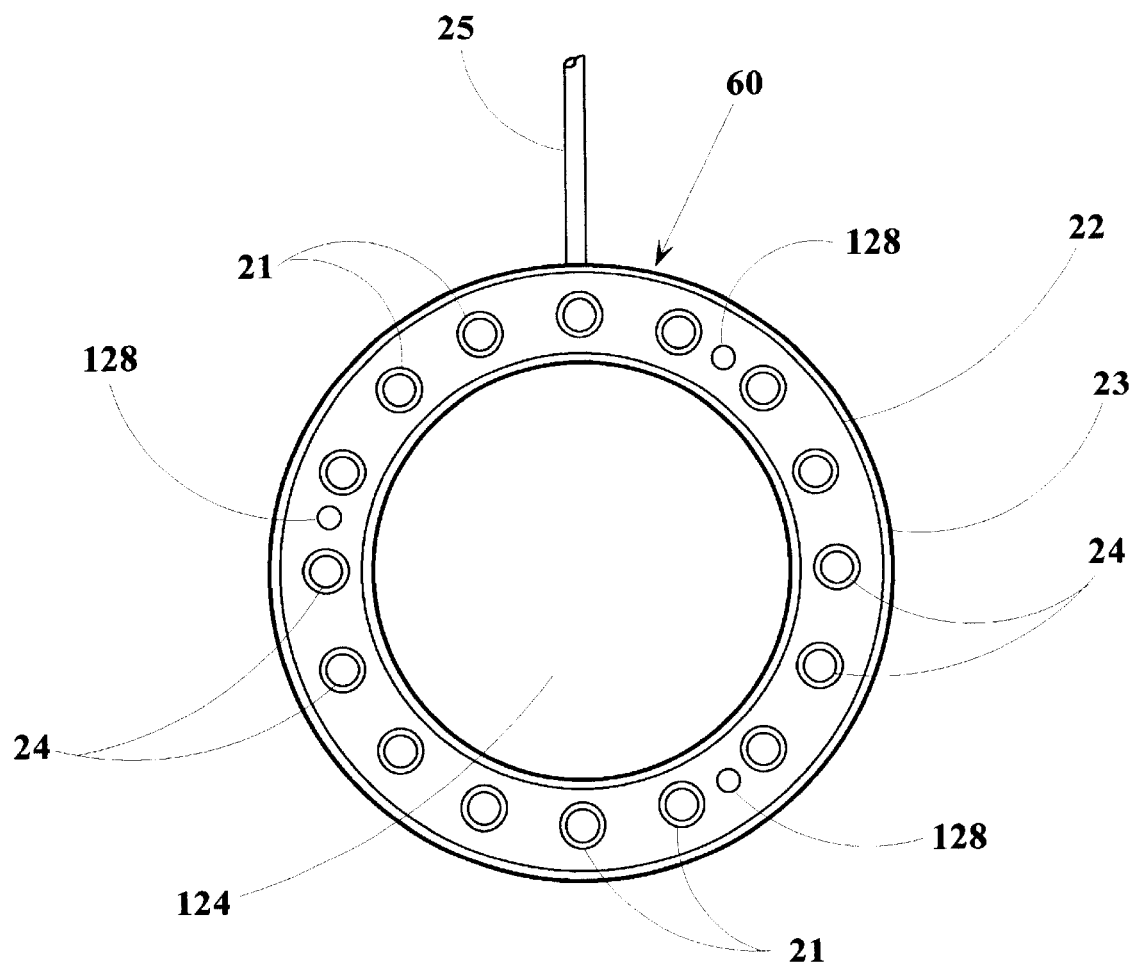
FIG. 2C is a schematic, upwardly-directed, view taken on line 2—2 in FIG. 2B.

FIG. 2C describes an upward-directed view of corneal illuminator 60. Corneal illuminator 60 includes an illuminating device in the form of ring illuminator housing 22 constructed and arranged to be mounted on the base of refractive surgery system operating microscope 20 (FIG. 2B). In the illustrated embodiment a set of mounting fasteners 126 (FIG. 2D) are used to mount corneal illuminator 60 to refractive surgery system operating microscope 20 (FIG. 2B) through a plurality of mounting holes 128, although other mounting methods may be used. Ring illuminator housing 22 is in the form of a continuous ring having an inner diameter generally sufficient to ensure an adequate clearance space 124 (FIG. 2C) so as not to interfere with the delivered laser beam or the optical view of the surgeon. In the illustrated embodiment, the inner diameter is approximately 60-mm. Ring illuminator housing 22 contains a plurality of annularly arranged openings 21 that are evenly or randomly spaced around ring illuminator housing 22, from which light source beams 26 emerge to illuminate cornea 28 (FIG. 2B). Illumination light sources 24 preferably comprise a plurality of infrared light emitters, although any monochromatic light source wavelength is applicable, which may be fiber bundles, light emitting diodes, etc. It has been determined that for the disclosed embodiment, sixteen near-infrared (840 to 930-nm) light emitting diodes serve as illumination light sources 24, and when spaced evenly around ring illuminator housing 22, provide sufficient illumination for the corneal striae detection algorithm, although more or less illumination light sources 24 may be employed. Corneal illuminator interface cable 25 connects corneal illuminator 60 to corneal illuminator electronics interface subsystem 58 (FIGS. 1, 3). Diffuser cover 23, containing a diffusing material particular to the monochromatic wavelength used, is mounted over illumination light sources 24 and attaches to ring illuminator housing 22. For the disclosed embodiment a Tech Spec™ linear polarizing laminated film is preferred.

Figure 2D:
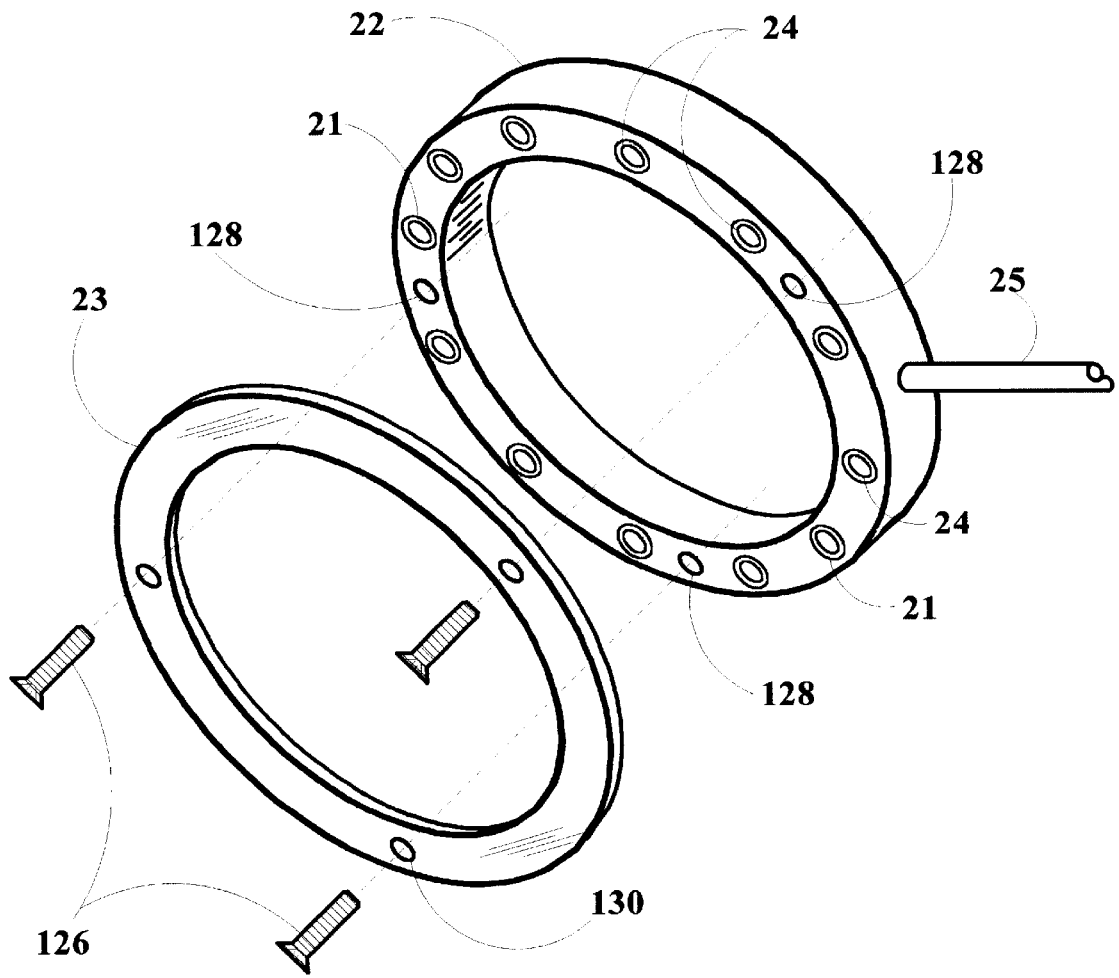
FIG. 2D is a perspective view describing the diffuser cover and its attachment to the corneal illuminator.

FIG. 2D describes a perspective view of diffuser cover 23 in relationship to ring illuminator housing 22. Diffuser cover 23 attaches to the bottom of ring illuminator housing 22 by the same mounting fasteners 126 used to mount corneal illuminator 60 to refractive surgery system operating microscope 20 (FIG. 2B) through mounting holes 128, although other methods of mounting diffuser cover 23 exist.

Figure 2E:
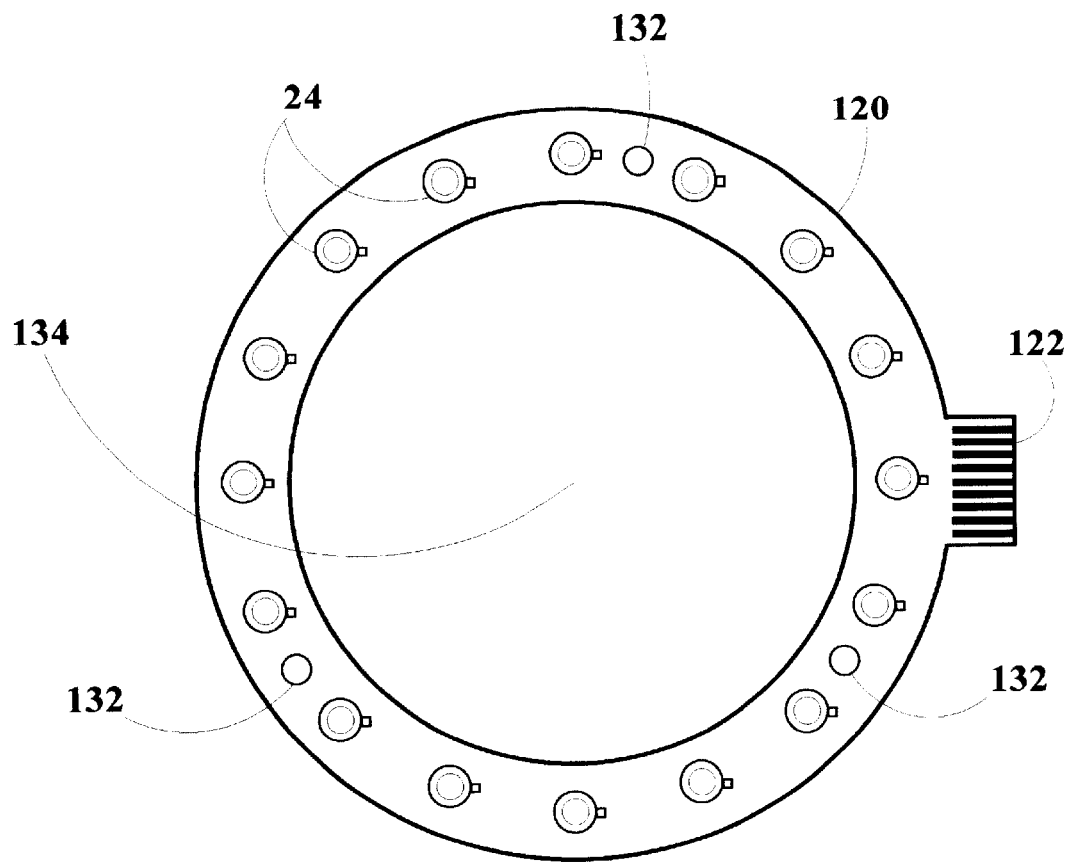
FIG. 2E shows a printed circuit board with illumination light sources installed and interface cable connector port.
Figure 8:
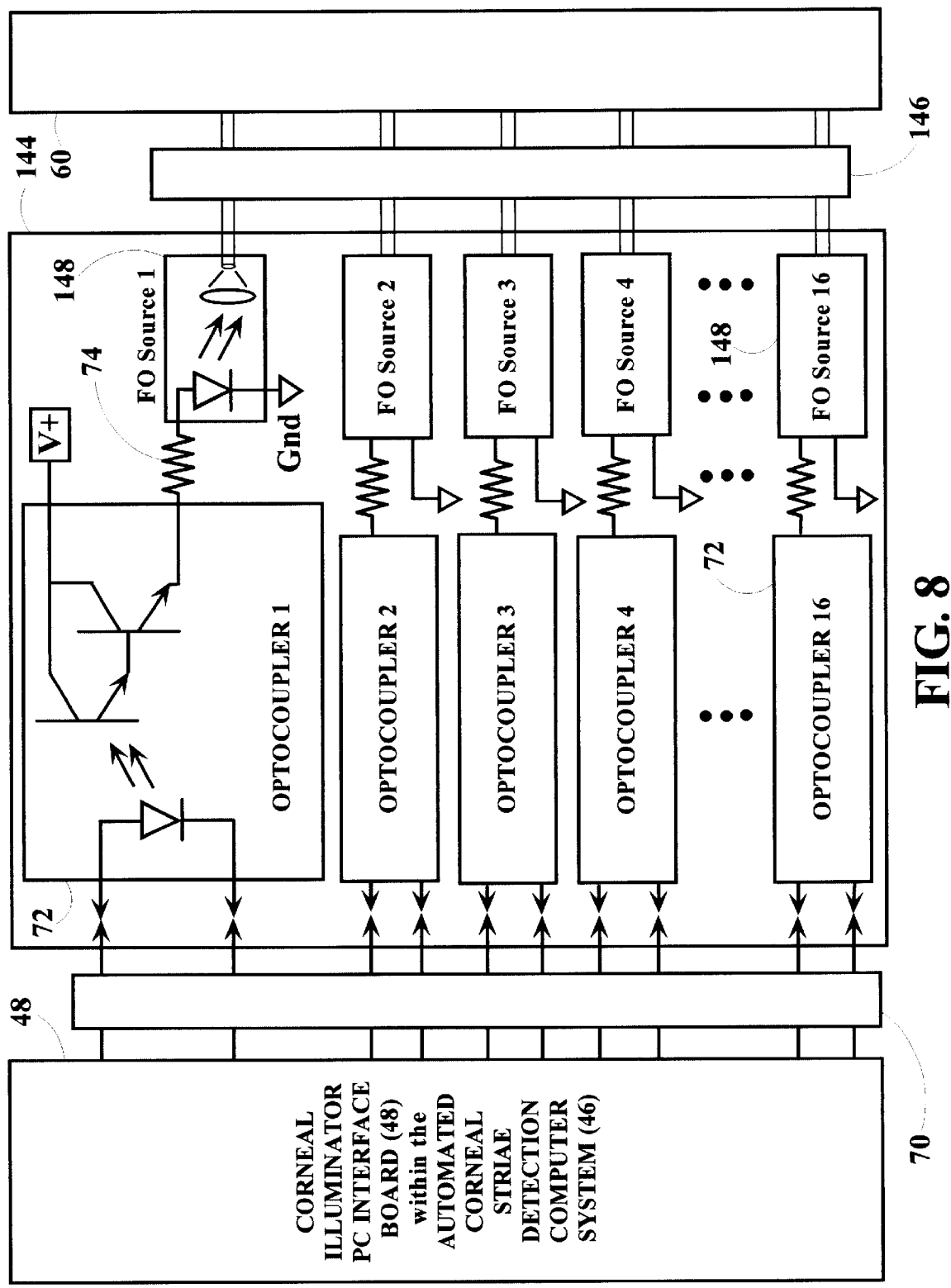
FIG. 8 shows a schematic view of an alternative corneal illuminator electronics interface subsystem using fiber optic illumination.

FIG. 2E describes the preferred electrical connection of illumination light sources 24 [preferably near-infrared (840 to 930-nm) light emitting diodes, although any monochromatic wavelength will suffice] to corneal illuminator interface cable 25 (FIG. 2B), for this disclosed embodiment of the invention. The near-infrared light emitting diodes are connected to an illumination light source printed circuit board 120. The printed circuit board has a large clearance hole 134 in the center so as not to interfere with the delivered laser beam or the optical view of the surgeon. Corneal illuminator interface cable 25 (FIG. 2D) connects to illumination light source printed circuit board 120 at an illuminator interface connector port 122, shown here as an edge card connector arrangement although other connector arrangements may be used, and to corneal illuminator electronics interface subsystem 58 (FIG. 3). Alternatively, illumination light sources 24, preferably near-infrared (840 to 930-nm) light emitting diodes in the preferred embodiment, may be individually wired to corneal illuminator interface cable 25 (FIG. 2B) which connects to corneal illuminator electronics interface subsystem 58. Even further, illumination light sources 24 may be individual fiber optic cables connected to an alternative fiber optic corneal illuminator electronics interface subsystem 144 (FIG. 8) through a fiber optic corneal illuminator interface bundle 146 (FIG. 8).

FIG. 3 describes corneal illuminator electronics interface subsystem 58 connected by corneal illuminator interface cable 25 to corneal illuminator 60 and by interface cable 70 to corneal illuminator PC interface board 48. Optocouplers 72, e.g., a Toshiba TLP371, couple the control signals from corneal illuminator PC interface board 48 to illumination light sources 24, preferably near-infrared (840 to 930-nm) light emitting diodes, although any monochromatic light source is applicable, through electrical current limiting resistors 74 and corneal illuminator interface cable 25.

Figure 4:
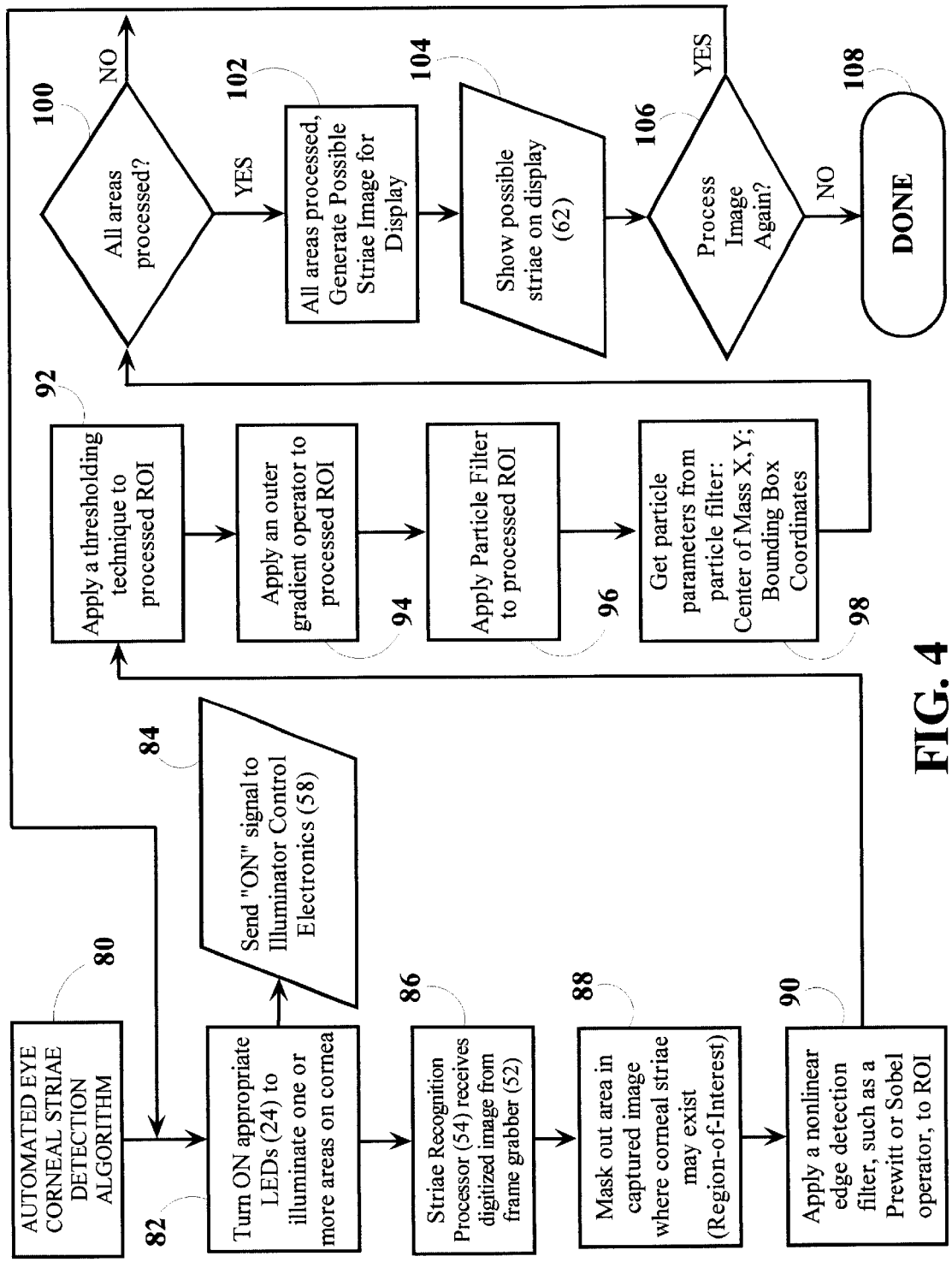
FIG. 4 is a flow chart describing the process of the invention.

FIG. 4 shows the preferred embodiment of the eye corneal striae detection algorithm in flowchart form. This algorithm will be described in detail later.

FIG. 5 describes four of the possible sixteen illumination coverage areas on cornea 28 of the preferred disclosed embodiment of the invention. Shown are the illumination light sources' illumination coverage areas: an illumination coverage area one 30, an illumination coverage area two 32, an illumination coverage area three 34, an illumination coverage area four 36, etc., etc., on a corneal surface within a region-of-interest (ROI) 136 slightly larger than the largest LASIK incision. In the present embodiment region-of-interest (ROI) 136 is approximately 15-mm in diameter and is centered on a pupil 27, although other ROI sizes can be used. Eye 29, an iris 31 and pupil 27 are shown in relationship to the illumination light sources' coverage areas.

Preferred Embodiments—Operation

The present invention is placed into operation after the LASIK surgery procedure is completed and the flap has been manipulated back to its original place by the surgeon and allowed to seal. According to FIG. 4, at 82, automated eye corneal striae detection computer system 46 sends out a control signal at 84 through corneal illuminator PC interface board 48 to corneal illuminator electronics interface subsystem 58 to illuminate illumination coverage area one 30 on cornea 28 with monochromatic light (FIG. 5), preferably near-infrared in the disclosed embodiment, although other monochromatic wavelengths may be used.

According to FIG. 1, video camera optical port 42 to which video camera 44 is coupled is typically a microscope beam splitter optical port which permits users to attach cameras thereto for recording the surgery and audience viewing of the surgery. Automated eye corneal striae detection computer system 46 takes advantage of one of these microscope beam splitter optical ports in order to monitor the eye via a provided video camera. For example, in the VISX™ laser system, an electronic output signal port connector is provided which is attached to an internal CCD camera. On other systems an electronic signal splitter can be attached at the output of the camera so the signal may be captured by video camera interface 50 and frame grabber 52. Alternatively, a separate camera may be provided with the automated eye corneal striae detection system of the invention and added to the microscope beam splitter optical port in order to capture the corneal images. That is, a number of methods and systems may be utilized to capture the image of the eye from refractive surgery system operating microscope 20 used in performing the refractive laser surgery. Frame grabber 52 takes the signal from video camera interface 50 and converts it to a digital signal. Alternatively, a digital camera and associated digital frame grabber, e.g., a Pulnix TM-1300 and National Instruments PCI-1424, respectively, can be used to capture the corneal image directly in digital format.

In FIG. 4, automated eye corneal striae detection computer system 46 receives the digitized image signal at 86 and converts the digitized image signal to a digital matrix for processing. Generally, automated eye corneal striae detection computer system 46 (1) processes the digitized corneal image for eye corneal striae recognition, (2) determines a position and a shape characteristic profile for each detected eye corneal striae object, and (3) displays the detected eye corneal striae object to surgeon's video display 62 (FIG. 1). Each of the functions of automated eye corneal striae detection computer system 46 are preferably performed by an algorithm carried out by eye corneal striae recognition processor 54, and will now be described in more detail.

Once the digitized eye corneal image is received at 86 there are several image processing methods that can be used to find eye corneal striae. One preferred method implemented by eye corneal striae recognition processor 54 uses the contrast between the eye corneal striae edge and the surrounding, normally smooth, corneal tissue to detect the striae and then determine the striae's position and shape characteristic profile by the following nine steps.

First, a small area of the captured image is masked out at 88 so as to limit region-of-interest (ROI) 136 (FIG. 5) for detecting the eye corneal striae. This region of interest is slightly larger than the LASIK incision, and in the present embodiment consists of a 15-mm diameter circular area centered on pupil 27 (FIG. 5).

Second, region-of-interest (ROI) 136 image data (FIG. 5) is then processed at 90 by an edge detection operator, preferably a Prewitt or Sobel, although other edge detection approaches can be used, to highlight edges within the ROI image. Once this operation has been performed, a bimodal image is produced.

Third, a threshold function is applied to the bimodal image at 92 to create a binary representation of the image which permits faster image processing. The threshold function replaces the image intensity values below some threshold value to black (a value of zero) while placing the intensity values above the threshold value to all white (a value of 256 in an 8-bit image representation), i.e., a binary representation of the image is created. At this step the edges within the ROI image are now totally white against a black background.

Fourth, the binary representation is preferably further processed at 94 by an outer gradient operator. In this operation an external edge algorithm subtracts the source ROI image from a dilated image of the source ROI image. The remaining image pixels correspond to the pixels added by the dilation. This yields a more pronounced image of the edges of the striae objects that remain after the edge enhancement operation 90 and thresholding function 92.

Fifth, at 96, the processed binary ROI image undergoes a characterization process, termed a particle filter, to determine a set of parametric values from the image. Since all eye corneal striae will have nearly the same size and shape characteristics, e.g., eye corneal striae will not be circular in shape, the search of the binary objects can be limited to a range defined by eye corneal striae dimensions and shape characteristics. A search is then performed on the binary image for objects matching the criterion. Those objects found in this range are returned with several pieces of shape characteristic information, termed a shape characteristic profile.

Sixth, at 98, the shape characteristic information (particle parameters) is extracted from the particle filter and saved for future display. Such pieces of shape information include, but are not limited to, Object Position, Center of Mass, Bounding Box coordinates, Perimeter length, etc.

Seventh, at 100, the algorithm decides whether all illumination coverage areas have been processed. In the preferred embodiment there would be sixteen such areas processed, although there could be more or less areas. If all areas have not been processed the algorithm returns to 82 to begin the next illumination coverage area process. FIG. 5 describes one possible method where the illumination coverage areas are scanned in a clockwise direction beginning at the 6 o'clock position (illumination coverage area one 30). After illumination coverage area one 30 is processed, illumination coverage area two 32 is processed followed by illumination coverage area three 34, etc., etc., until all areas have been processed. Other corneal scanning approaches can also be used. For example, two adjacent areas, e.g., illumination coverage area one and illumination coverage area two could be illuminated at the same time by sending appropriate control signals at 84 (FIG. 4) through corneal illuminator PC interface board 48 and corneal illuminator electronics interface subsystem 58 (FIG. 1); or random areas may be scanned by sending appropriate control signals at 84. If all areas have been processed, the algorithm then continues on to display the results.

Eighth, at 102, the monochrome (black and white) binary eye corneal striae image is enhanced by outlining possible striae found in 96 and 98 with a high-contrast color, such as red, yellow or green, although other high-contrast colors would suffice, so that the possible corneal striae are obvious to the surgeon. This new generated image is then sent to surgeon's video display 62 (FIG. 1) for viewing by the surgeon.

Ninth, at 106, the surgeon is given the option to repeat the process. This may occur after the surgeon has smoothed a striae or wrinkle, or when the surgery procedure is complete. If the surgeon requires another process, algorithm control is sent back to 82 and the procedure repeats. If the surgeon indicates the procedure is complete, the algorithm is finished at 108.

Other Embodiments
Additional Video Camera Position—Description

Figure 6:
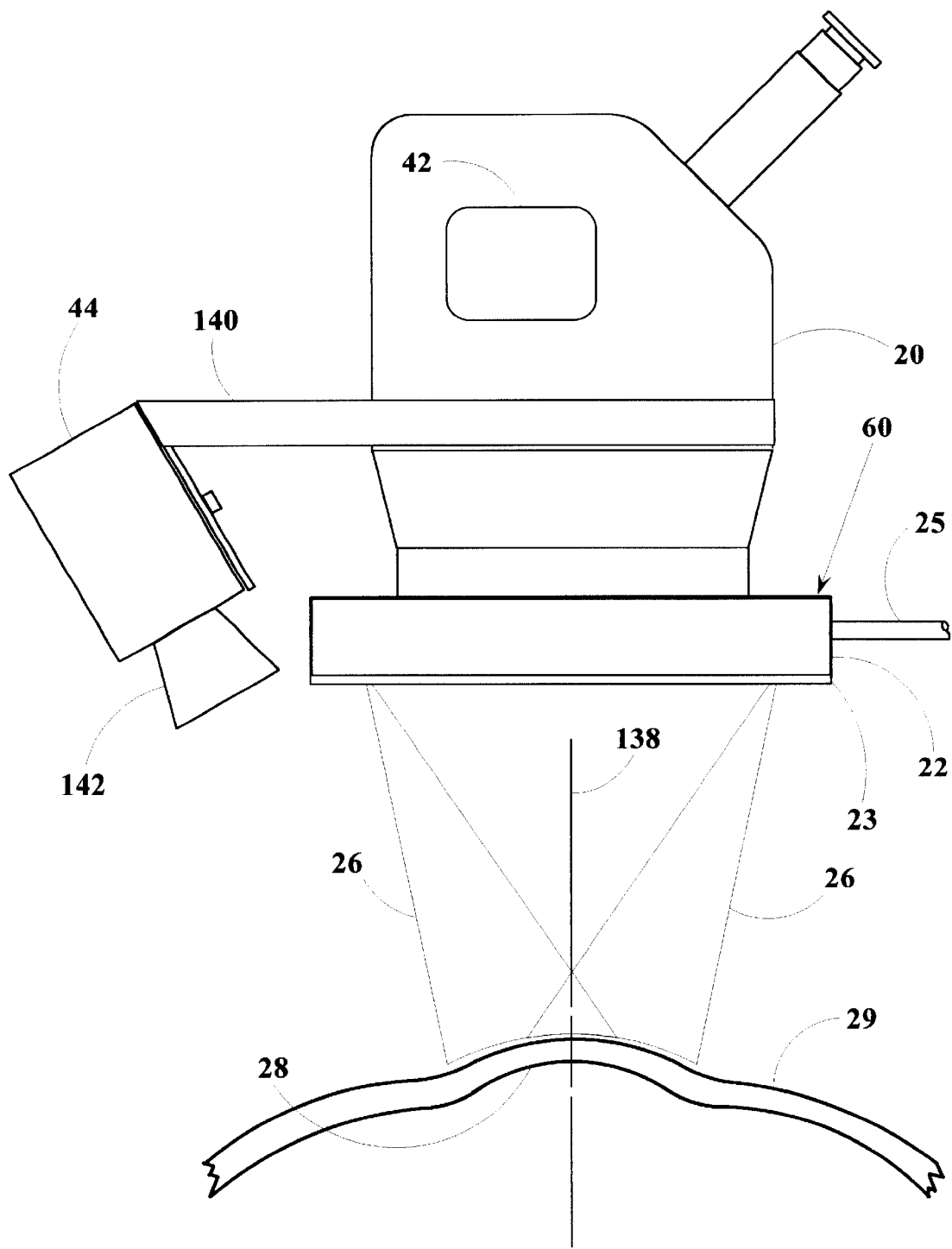
FIG. 6 is an alternate video camera position and attachment method.

FIG. 6 describes an additional embodiment for the position of video camera 44. Video camera 44 is shown mounted to refractive surgery system operating microscope 20 by a mounting bracket 140 at an appropriate angle to capture an image of the cornea and at a proper position so as not to interfere with the surgeon or surgeon's assistants. A video camera lens 142 is used to provide automated eye corneal striae detection computer system 46 (FIG. 1) with an appropriate sized image to perform striae detection.

Additional Video Camera Position—Operation

Turning to FIG. 6, video camera 44 is shown mounted separate from refractive surgery system operating microscope 20. This embodiment provides automated eye corneal striae detection computer system 46 with a cornea image for eye corneal striae detection. The addition of video camera lens 142 ensures that eye corneal striae recognition processor 54 receives a similar image as is delivered in the previous embodiment. In this embodiment the output port of video camera 44 is connected to video camera interface 50 in automated eye corneal striae detection computer system 46 through video camera cable 150 as before.

Another Eye Corneal Striae Recognition Approach—Description

Figure 7:
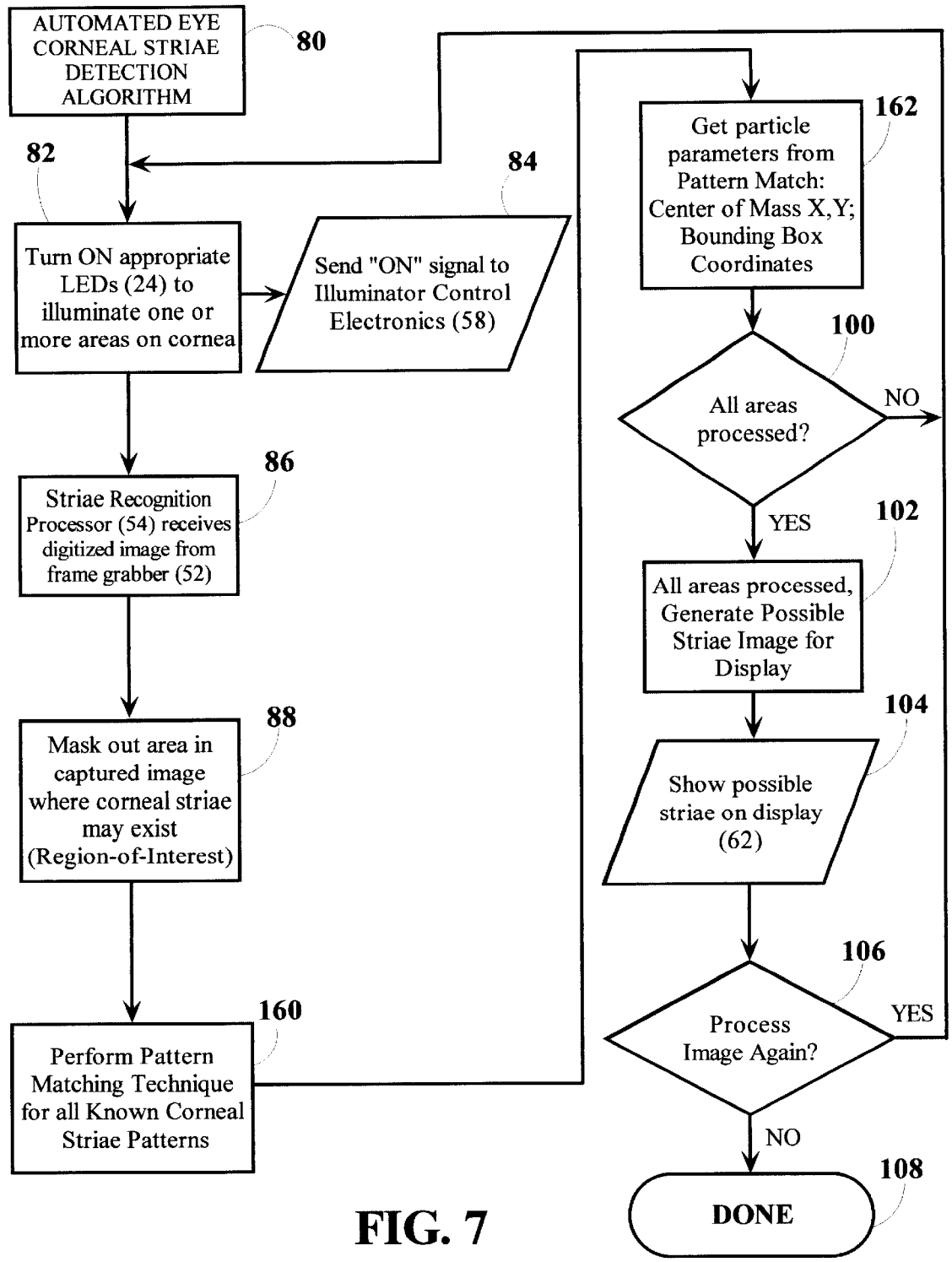
FIG. 7 is an alternate striae recognition algorithm.

FIG. 7 describes an alternative eye corneal striae recognition approach. Details of this algorithm are discussed below.

Another Eye Corneal Striae Recognition Approach—Operation

Turning now to FIG. 7, another eye corneal striae recognition technique, involving pattern matching, is implemented at 160. As in the main embodiment, the cornea is illuminated at 82 and 84; the illuminated cornea image is captured through video camera 44 by video camera interface 50 and frame grabber 52 at 86; the possible corneal area (ROI) for striae is masked out at 88; and a pattern matching technique is applied at 160. This alternative pattern matching technique uses a grayscale pattern matching method based on correlation. Known recorded eye corneal striae patterns are scanned through the ROI image searching for a pattern match. The technique is shift-invariant, stretch or size-invariant, and rotation-invariant, and is highly immune to adverse lighting conditions, focus variations, or noise. Once a striae object is found, its shape characteristic information (particle parameters), such as Object Position, Center of Mass and Bounding Box coordinates, are saved at 162 as in the main embodiment algorithm, and display continues as before at 102 and 104. Algorithm control continues from here as described in the main embodiment.

Alternate Illumination Source—Description

FIG. 8 describes an alternative fiber optic corneal illuminator electronics interface subsystem 144 connected by a fiber optic corneal illuminator interface bundle 146 to corneal illuminator 60 and by an interface cable 70 to corneal illuminator PC interface board 48. Optocouplers 72, e.g., a Toshiba TLP371, couple the control signal from corneal illuminator PC interface board 48 to fiber optic illumination light sources 148, e.g., an AMP 269110-1, preferably near-infrared wavelengths (840 to 930-nm), although any monochromatic light source is applicable, through electrical current limiting resistors 74 and fiber optic corneal illuminator interface bundle 146.

Alternate Illumination Source—Operation

This embodiment of the present invention is placed into operation after the LASIK surgery procedure is completed and the flap has been manipulated back to its original place and allowed to seal. According to FIG. 4, at 82, automated eye corneal striae detection computer system 46 (FIG. 1) sends out a control signal at 84 through corneal illuminator PC interface board 48 to alternative fiber optic corneal illuminator electronics interface subsystem 144 to illuminate illumination coverage area one 30 on cornea 28 (FIG. 5) with monochromatic light via fiber optic means, preferably near-infrared wavelengths (840 to 930-nm) in the disclosed embodiment although other monochromatic wavelengths may be used. Algorithm control continues from here as described in the main embodiment.

Conclusions, Ramifications, and Scope

From the embodiments of the invention described above it can be appreciated that the automated eye corneal striae detection system provides a very effective method for detecting eye corneal striae, or wrinkles, that may be present after LASIK refractive surgery. Since the automated eye corneal striae detection system actually detects and displays eye corneal striae, it offers several advantages over current methods aimed at only preventing striae. Additionally, the automated eye corneal striae detection system provides detection of striae from several different angles thereby offering superior corneal coverage over current manual techniques that use only two or three angles.

While the invention has been described in accordance with what is presently considered to be the preferred embodiments, it is to be understood that the invention is not limited to the disclosed embodiments, but on the contrary, is intended to cover various modifications and equivalent arrangements. Thus, while particular functional systems have been disclosed, it will be appreciated that other functional systems may be used as well. That is, the striae recognition processor and corneal illuminator electronics interface subsystem may be combined in a single system or further divided to perform the required tasks of the invention. Furthermore, while a particular preferred method, and an alternative method, have been disclosed for striae detection, it will be appreciated that other algorithms may be used. For example, neural network processing techniques, which are very efficient at pattern matching, could be used.

Additionally, as only one video camera has been shown, it will be appreciated that two or more video cameras could be implemented to offer an increase in processing speed as well as additional information about striae object parameters, such as height information, etc. It will therefore be appreciated by those skilled in the art that yet other modifications could be made to the provided invention without deviating from its spirit and scope as so claimed.

What is claimed is:

1. An automated eye corneal striae recognition system, comprising:
    a) means for illuminating an eye cornea with light;
    b) means for capturing an image of the illuminated eye cornea; and
    c) a computer system including,
        (i) means for controlling said means for illuminating said eye cornea,
        (ii) means for receiving said image of the eye cornea from said means for capturing said image, and
        (iii) a processor means for
            (A) processing said image,
            (B) detecting a corneal stria object from the processed image if a corneal stria is present, and
            (C) determining a respective position of the detected corneal stria object relative to the eye cornea.

2. An automated eye corneal striae recognition system according to claim 1, wherein:
    said means for illuminating said eye cornea includes,
        (i) a housing adapted to be fastened to the lower end of a microscope, said housing having a plurality of annularly arranged spaced openings adapted to direct light away toward said eye cornea,
        (ii) a supporting means within said housing for supporting a source of a light beam at each of said openings,
        (iii) a diffuser means for diffusing each said source of a light beam, and
        (iv) means for controlling each said source of a light beam individually.

3. An automated eye corneal striae recognition system according to claim 2, wherein:
    said housing is a generally continuous ring.

4. An automated eye corneal striae recognition system according to claim 2, wherein:
    each said source of a light beam is a light emitting diode.

5. An automated eye corneal striae recognition system according to claim 4, wherein:
    said supporting means for each said light emitting diode within said housing is a printed circuit board.

6. An automated eye corneal striae recognition system according to claim 4, wherein:
    said means for controlling each said light emitting diode provides appropriate electrical current amperage to each said light emitting diode.

7. An automated eye corneal striae recognition system according to claim 2, wherein:
    each said source of a light beam is an individual light transmitting fiber optic cable conveying light from an external source.

8. An automated eye corneal striae recognition system according to claim 7, wherein:
    said external source is a light emitting diode coupled to said light transmitting fiber optic cable.

9. An automated eye corneal striae recognition system according to claim 8, wherein:
    said means for controlling each said light emitting diode provides appropriate electrical current amperage to each said light emitting diode.

10. An automated eye corneal striae recognition system according to claim 2, wherein:
    said light has a wavelength, and said diffuser means is a polarizer selected for said wavelength.

11. An automated eye corneal striae recognition system according to claim 1, wherein:
    said light is a monochromatic light.

12. An automated eye corneal striae recognition system according to claim 1, wherein:
    said means for receiving said image of the eye cornea is an analog video camera.

13. An automated eye corneal striae recognition system according to claim 12, wherein:
    said analog video camera is attached to an optical port of a microscope of a refractive laser surgery system.

14. An automated eye corneal striae recognition system according to claim 13, further comprising:
    a bracket adapted to fasten said analog video camera to said microscope of said refractive laser surgery system.

15. An automated eye corneal striae recognition system according to claim 14, further comprising:
    an imaging lens attached to said analog video camera.

16. An automated eye corneal striae recognition system according to claim 12, wherein:
    said image of the eye cornea is a digital image.

17. An automated eye corneal striae recognition system according to claim 16, wherein:
    said means for receiving said digital image of the eye cornea from said analog video camera is an analog frame grabber.

18. An automated eye corneal striae recognition system according to claim 1, wherein:
    said means for receiving said image of the eye cornea is a digital video camera.

19. An automated eye corneal striae recognition system according to claim 18, further comprising:
    a refractive laser surgery system including a microscope having a video camera optical port, said digital video camera being coupled to said port.

20. An automated eye corneal striae recognition system according to claim 19, wherein:
    a bracket adapted to fasten said digital video camera to said microscope of said refractive laser surgery system.

21. An automated eye corneal striae recognition system according to claim 18, further comprising:
    an imaging lens attached to said digital video camera.

22. An automated eye corneal striae recognition system according to claim 18, wherein:
    said image is a digital image.

23. An automated eye corneal striae recognition system according to claim 22, wherein:
    said means for receiving said digital image of the eye cornea from said digital video camera is a digital frame grabber.

24. An automated eye corneal striae recognition system according to claim 1, wherein:
    said processor means determines shape characteristics of each said detected corneal stria object.

25. An automated eye corneal striae recognition system according to claim 1, wherein:
    said processor means detects said corneal stria by selecting a limited region-of-interest area in said image where said corneal stria object may be present.

26. An automated eye corneal striae recognition system according to claim 25, wherein:
said processor means applies a corneal stria detection algorithm to said limited region-of-interest area in said image.

27. An automated eye corneal striae recognition system according to claim 26, wherein:
said processor means detects said corneal stria object by further applying a means for enhancing corneal stria edges.

28. An automated eye corneal striae recognition system according to claim 27, wherein:
said processor means enhances said corneal stria edges by increasing the contrast between a corneal stria object and normal corneal tissue surrounding said corneal stria in said image.

29. An automated eye corneal striae recognition system according to claim 28, wherein:
said image includes a plurality of intensity values, and the contrast is increased by said processor means applying an edge detection operator to the intensity values in said image to produce a bimodal histogram of the intensity values.

30. An automated eye corneal striae recognition system according to claim 29, wherein:
said processor means detects said corneal stria object by further applying a threshold function to said bimodal histogram to create a binary representation of said image.

31. An automated eye corneal striae recognition system according to claim 30, wherein:
said processor means detects said corneal stria object by further applying an outer gradient operator to said binary representation.

32. An automated eye corneal striae recognition system according to claim 30, wherein:
said processor means searches said binary representation for an object having a size within a size range of a set of corneal striae objects.

33. An automated eye corneal striae recognition system according to claim 30, wherein:
said processor means processes said binary representation to ensure that said object, within said size range of said set of corneal striae objects, possesses corneal striae shape attributes.

34. An automated eye corneal striae recognition system according to claim 25, wherein:
said processor means searches said limited region-of-interest area in said image for objects correlating highly with one of several known corneal striae object patterns.

35. An automated eye corneal striae recognition system according to claim 1, further comprising:
d) display means for displaying indications of said detected corneal stria object.

36. An automated eye corneal striae recognition system according to claim 1, wherein:
said processor means saves a position indication of said respective position of each corneal stria object detected in said image.

37. An automated eye corneal striae recognition system according to claim 36, wherein:
said processor means determines and saves shape characteristic profile information for each detected corneal striae object in said image.

38. An automated eye corneal striae recognition system according to claim 37, further comprising:
d) display means for displaying indications of said detected corneal stria object,
wherein said processor means uses said saved position indications and said shape characteristic profile information for each detected corneal stria object to highlight each said corneal stria object in said image on said display means.

39. An automated eye corneal striae recognition system according to claim 38, wherein:
said display means is a high contrast video display, and said processor means highlights each said detected corneal stria object in said image by outlining each said detected corneal stria object with a high contrast color.

40. An automated eye corneal striae recognition system according to claim 1, further comprising:
d) display means for displaying indications of said detected corneal striae object,
wherein said computer system includes a means for sending a video signal, and wherein when each said corneal stria object is detected and highlighted, said means for sending said video signal sends a video signal containing each highlighted corneal stria object to said display means.

41. An automated eye corneal striae recognition system according to claim 1, further comprising:
d) a laser generator for performing refractive laser surgery on the eye cornea.

42. A method for automatically detecting corneal striae, said method comprising:
a) illuminating the eye cornea with light;
b) obtaining an image of said illuminated eye cornea;
c) processing said image;
d) determining from said processed image whether one or more corneal striae objects are present; and
e) if one or more corneal striae objects are present, determining the position of each said corneal stria object and providing an indication of the position of each said corneal stria object relative to the cornea.

43. A method according to claim 42, further comprising:
if one or more corneal striae objects are present, determining a shape of each said corneal stria object.

44. A method according to claim 43, further comprising:
providing an indication of the shape of each said corneal stria object.

45. A method according to claim 42, wherein:
said image is processed digitally.

46. A method according to claim 42, wherein:
said light is monochromatic light.

47. A method according to claim 42, wherein:
said light has a wavelength between 840 to 930 nm.

48. A method according to claim 42, wherein:
said processing includes
(i) defining a limited region-of-interest in said image for detecting the eye corneal striae objects,
(ii) processing image data from the limited region-of-interest by an edge detection operator such that a bimodal image is produced,
(iii) applying a threshold function to said bimodal image such that a binary representation of said image is created, and
(iv) searching the binary image for objects having corneal striae size and shape characteristics.

49. A method according to claim 48, further comprising:
(v) after applying the threshold function and before providing a characterization process, processing said binary representation by an outer gradient operator.

50. A method for automatically detecting corneal striae, said method comprising:
a) illuminating the cornea with a light beam directed toward the cornea at a first angle;
b) obtaining an image of the cornea;
c) processing said image;
d) determining from said processed image whether one or more corneal striae objects are present; and
e) repeating steps a)–d) with light beams directed toward the cornea at distinct angles.

51. A method according to claim 50, further comprising:
f) if one or more corneal striae objects are present, determining the position of each said corneal striae object and providing an indication of the position of each said corneal striae object relative to the cornea.

52. A method according to claim 50, wherein:
each said light beam is monochromatic.

53. A method according to claim 52, wherein:
each said light beam has a wavelength between 840 to 930 nm.

54. A method according to claim 50, wherein:
each said light beam is created by a light emitting diode.

55. A method according to claim 50, wherein:
each said light beam is a circular beam, and said beams are projected onto the cornea in a pattern in which each said light beam overlaps another said light beam.

56. A method according to claim 55, wherein:
said pattern is circular.

* * * * *